(12) United States Patent
Bear et al.

(10) Patent No.: US 9,235,690 B2
(45) Date of Patent: *Jan. 12, 2016

(54) MEDICATION DISPENSER WITH INTEGRATED MONITORING SYSTEM

(71) Applicant: SentiCare, Inc., Framingham, MA (US)

(72) Inventors: David M. Bear, Wellesley, MA (US); Yogendra Jain, Wellesley, MA (US)

(73) Assignee: SentiCare, Inc., Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/076,482

(22) Filed: Nov. 11, 2013

(65) Prior Publication Data

US 2014/0188272 A1  Jul. 3, 2014

Related U.S. Application Data

(63) Continuation of application No. 13/269,981, filed on Oct. 10, 2011, now Pat. No. 8,583,281, which is a continuation of application No. 11/943,451, filed on Nov. 20, 2007, now Pat. No. 8,060,249.

(60) Provisional application No. 60/866,916, filed on Nov. 22, 2006.

(51) Int. Cl.
G06F 17/00 (2006.01)
G06F 19/00 (2011.01)
A61J 7/04 (2006.01)

(52) U.S. Cl.
CPC ........... *G06F 19/3462* (2013.01); *A61J 7/0481* (2013.01); *A61J 2007/0418* (2013.01); *A61J 2007/0454* (2013.01); *A61J 2200/30* (2013.01)

(58) Field of Classification Search
CPC ....................................... A61J 7/0481
USPC .......................... 700/244, 231, 232, 236, 241
See application file for complete search history.

(56) References Cited

U.S. PATENT DOCUMENTS

| | | |
|---|---|---|
| 4,617,557 A | 10/1986 | Gordon |
| 4,674,652 A | 6/1987 | Aten et al. |
| 4,943,939 A | 7/1990 | Hoover |
| 5,412,372 A | 5/1995 | Parkhurst et al. |
| 5,502,944 A | 4/1996 | Kraft et al. |
| 5,646,912 A | 7/1997 | Cousin |

(Continued)

OTHER PUBLICATIONS

International Search Report and Written Opinion for International Application PCT/US07/85307 mailed Jul. 18, 2008.

(Continued)

*Primary Examiner* — Michael K Collins
(74) *Attorney, Agent, or Firm* — Ash Tankha; Lipton, Weinberger & Husick

(57) ABSTRACT

Devices, systems, and methods are provided for remote visualization of the storage compartments in a medication dispenser device, to monitor a patient's compliance with a medication dosage schedule and for verifying the proper loading of medication into the patient's medication dispenser device. The device may include a plurality of storage compartments, each having an interior space for storing at least one medication or medication reminder marker; an image capturing device (e.g., a camera) positionable to capture an image of the interior space of each storage compartment; and a communications module for electronically transmitting the captured image to a central monitoring station.

20 Claims, 4 Drawing Sheets

(56) References Cited

U.S. PATENT DOCUMENTS

| | | | |
|---|---|---|---|
| 5,752,621 | A | 5/1998 | Passamante |
| 6,324,253 | B1 | 11/2001 | Yuyama et al. |
| 6,411,567 | B1 | 6/2002 | Niemiec et al. |
| 6,471,087 | B1 | 10/2002 | Shusterman |
| 6,574,166 | B2 | 6/2003 | Niemiec |
| 6,581,798 | B2 | 6/2003 | Liff et al. |
| 6,611,733 | B1 | 8/2003 | De La Huerga |
| 6,662,081 | B1 | 12/2003 | Jacober et al. |
| 6,771,174 | B2 | 8/2004 | Broas |
| 6,961,285 | B2 | 11/2005 | Niemiec et al. |
| 7,218,992 | B2 | 5/2007 | Wang et al. |
| 7,440,817 | B2 | 10/2008 | Fu |
| 7,502,666 | B2 | 3/2009 | Siegel et al. |
| 7,570,786 | B2 | 8/2009 | Ateya |
| 7,630,788 | B1 | 12/2009 | Reese |
| 7,689,318 | B2 | 3/2010 | Draper |
| 8,060,249 | B2 * | 11/2011 | Bear et al. ............ 700/244 |
| 8,068,931 | B2 * | 11/2011 | Tran et al. ............ 700/236 |
| 8,583,281 | B2 * | 11/2013 | Bear et al. ............ 700/244 |
| 2003/0216831 | A1 | 11/2003 | Hart et al. |
| 2005/0216120 | A1 | 9/2005 | Rosenberg et al. |
| 2005/0224510 | A1 | 10/2005 | Remis et al. |
| 2005/0240305 | A1 | 10/2005 | Bogash et al. |
| 2005/0252924 | A1 | 11/2005 | Pieper et al. |
| 2006/0015536 | A1 | 1/2006 | Buchanan et al. |
| 2006/0154642 | A1 | 7/2006 | Scannell |
| 2007/0016443 | A1 | 1/2007 | Wachman et al. |
| 2007/0185615 | A1 | 8/2007 | Bossi et al. |
| 2008/0047969 | A1 | 2/2008 | Farhan et al. |
| 2008/0105588 | A1 * | 5/2008 | Tran et al. ............ 206/534 |
| 2008/0119958 | A1 | 5/2008 | Bear et al. |
| 2008/0179387 | A1 | 7/2008 | Cantlay et al. |
| 2008/0300719 | A1 * | 12/2008 | Duke ............ 700/244 |
| 2009/0134181 | A1 | 5/2009 | Wachman et al. |

OTHER PUBLICATIONS

"Epiccl Medication Reminders: Pill Dispenser, Vibrating Watch, Medication Timer, Alarm Watch," http://www.epill.com.

* cited by examiner

MEDICATION DISPENSER WITH INTEGRATED MONITORING SYSTEM

CROSS-REFERENCE TO RELATED APPLICATIONS

This is a continuation of U.S. application Ser. No. 13/269,981, filed Oct. 10, 2011, which is a continuation of U.S. application Ser. No. 11/943,451, filed Nov. 20, 2007, which claims priority to and the benefit of U.S. Provisional Application No. 60/866,916, filed Nov. 22, 2006. The applications are incorporated herein by reference in their entirety.

BACKGROUND

Patient compliance with medication dosing schedules is a serious problem. Approximately 60% of prescribed medication is not taken as directed. Non-compliance leads to worsening illness, hospitalization, irreversible loss of function, and death, resulting in tremendous human and financial costs. When medicines are dispensed, especially outside hospitals, errors in selection of the correct pill and the appropriate dose add further morbidity and mortality.

For example, elderly patients and patients taking multiple medications at different dosing schedules may have difficulty remembering to take their medications at the scheduled times. Approximately 90% of elderly patients make medication errors, 35% of which are serious. Approximately 40% of all hospital admissions among elderly patients are due to medication problems.

Other medications, such as opioid analgesics and narcotics, may be prone to abuse or diversion, for instance taken in excess or diverted and sold to others who would abuse the medication. Groups of people in which non-compliance is a common problem include Americans with chronic disease, diabetes (approximately 18 million), cardiovascular diseases (approximately 58 million), depression (approximately 20 million), and asthma (approximately 17 million).

It would be desirable to enhance patient adherence to dosing schedules for prescription medications. It would be useful to provide a low-cost dispenser and monitoring system to verify that medications stored therein are not taken in excess (i.e., abused) and that vital medications doses are not skipped. It also would be useful to provide a dispenser and monitoring system to verify that medications stored therein are removed by the patient, or an authorized person, in order to prevent diversion.

SUMMARY

The present devices for the monitored storage and dispensing of medication comprise a plurality of storage compartments, wherein each storage compartment has an interior space for storing at least one medication or at least one medication reminder marker; an image capturing device positionable to capture an image of the interior space of each of the plurality of storage compartments; and a communications module for electronically transmitting the image captured by the image capturing device to a central monitoring station. In one embodiment, each storage compartment comprises a wall through which the image can be captured. In one embodiment, one or more of the storage compartments comprise a plurality of solid oral dosage forms of one or more medications. In another embodiment, the storage compartments comprise at least one medication reminder marker that comprises an object with a shape and color selected to match a shape and color code present on a label of a prescribed medication, such as an inhaler or a parenteral medication.

In certain embodiments, the plurality of storage compartments is provided in an array corresponding to the days of the week and periods of time throughout the day. In certain embodiments, the storage compartments are replaceably removable from the device, either in one unit or in two or more subunits of two or more storage compartments. In one embodiment, each subunit comprises compartments corresponding to at least one day of the week. In a preferred embodiment, the image capturing device comprises a camera. The camera may be a digital still camera or a digital video camera. A modified flat bed scanner, based on a linear array of CCD devices, could also be used for digital image capture. In certain embodiments, the communications module for electronically transmitting at least a portion of the captured image comprises a network link for a telephone line, power line, wireless gateway, or cellular network. The network link may, for example, comprise an embedded or dongle circuitry for WiFi, zigbee, powerline, or bluetooth transmission circuitry.

In one embodiment, the device includes an electronic communications component for communicating information to a user of the dispenser, from a user of the dispenser to the central monitoring station, or both to and from the user. The communications component may include at least one audio, visual, or tactile means for communicating information. For example, the information communicated to the user may include battery power level or other operational status information about the device, or information about the user's compliance with his or her medication dosage schedule. Information communicated from the user may include personal identity information of the user of the dispenser, e.g., for medication security purposes. In various other embodiments, the information comprises contact information for the patient's doctor, pharmacy, caregiver, or other emergency contact; music preference information; or weather, news, or sports information.

In another aspect, the present patient medication compliance monitoring systems comprise at least one visually monitored medication dispenser assigned to an individual patient having a medication dosage schedule, wherein the medication dispenser comprises a plurality of storage compartments, wherein each compartment has an interior space for storing at least one medication or at least one medication reminder marker, an image capturing device positionable to capture an image of the interior space of each of the plurality of compartments; and a communications module for electronically transmitting the image captured by the image capturing device to a central monitoring station; and a central monitoring station capable of receiving and viewing the image from the at least one medication dispenser. In one embodiment, the system comprises a plurality of visually monitored medication dispensers, wherein each medication dispenser is assigned to a different individual patient having a medication dosage schedule. In certain embodiments, the image capturing device comprises a camera. In certain other embodiments, the communications module for electronically transmitting the captured image comprises a network link for a telephone line, wireless gateway, or cellular network. The medication dispenser may further comprise at least one audio, visual, or tactile means for communicating information from the user of the dispenser to the central monitoring station. In certain other embodiments, the medication dispenser further comprises electronic means for receiving image capture instructions from the central monitoring station. The system may comprise the use of at least one computer.

In still another aspect, the present methods of monitoring a patient's compliance with the patient's medication dosage schedule comprise the steps of: receiving at a central monitoring station an image of an interior space of at least one medication storage compartment within a medication dispenser device which is associated with the patient and remote from the monitoring station; and determining from the image at the central monitoring station the presence or absence of at least one medication or medication reminder marker in said at least one medication storage compartment. In certain embodiments, the methods further comprise the step of: transmitting to the medication dispenser information regarding the patient's compliance with the medication dosage schedule. In certain other embodiments, the methods further comprise the step of: transmitting from the central monitoring station an instruction to the medication dispenser to capture an image at one or more selected times or to adjust the frequency of random capture of an image. In preferred embodiments, the received image is examined to determine whether the presence or absence of at least one medication or medication reminder marker matches that which is expected for the compartment according to the medication dosage schedule. In other preferred embodiments, the information transmitted to the medication dispenser device is visually displayed thereon and/or audibly broadcast therefrom. The information transmitted to the medication dispenser, in some embodiments, may be visually displayed or audibly broadcast from an auxiliary device. The auxiliary device may be selected from a home computer, land-line telephone, mobile telephone, or personal digital assistant device. In certain other embodiments, the methods further comprise the step of: transmitting information to a caregiver for the patient if the image captured does not match what is expected for the compartment of the medication dispenser device.

In yet another aspect, the present central station for medication compliance monitoring, comprises a memory for storing computer-executable instructions; and a processor in communication with the memory, wherein the memory is operable to execute the computer-executable instructions to: receive at least one image from a visually monitored medication dispenser; determine, based upon the received image, the presence or absence of at least one medication or medication marker according to a medication dosage schedule; and transmit compliance information to the medication dispenser based on the determination.

In still a further aspect, a method is provided for verifying proper loading of medication in a medication dispenser comprising the steps of: loading at least one medication or medication reminder marker into all or a subset of a plurality of medication storage compartments located in one or more containers for use in a medication dispenser device, according to a medication dosage schedule for a patient; instructing the medication dispenser to capture an image of the interior space of at least one of the medication storage compartments and to electronically transmit the image to a central monitoring station; and receiving information from the central monitoring station verifying whether the image corresponds to that which is expected for the medication storage compartment according to the medication dosage schedule. The container may be loaded with a plurality of solid oral dosage forms, medication reminder markers, or a combination thereof. The steps may be performed by the patient, or by an automated dispenser, a pharmacist, a caregiver for the patient, or remote operator guidance.

BRIEF DESCRIPTION OF THE FIGURES

FIG. 1A shows a top perspective view of one embodiment of the device in a closed position. FIG. 1B shows a perspective view of the same embodiment of the dispenser device in an open position, showing a three-by-seven array of storage compartments. Each storage compartment typically is capable of accommodating a plurality of medications or medication marker reminders. FIG. 1B shows a weekly dispenser with removable storage compartments for accommodating up to three dosage periods per day. Other variations of this dispenser design are envisioned, including monthly dispensers, bimonthly dispensers, and any of the foregoing with one, two, three, or four dosage periods per day. In one embodiment, the drug may be an opioid or other drug which may be prone to abuse, and dispenser may be for a greater number of days (e.g., a 30 day supply) than would typically be prescribed due to the risk of diversion or abuse with an unmonitored prescription supply. In the embodiment shown in FIG. 1B, the storage compartments are removable as a single unit or as two or more subunits that correspond to one or more days of the week. FIG. 1C shows a bottom perspective view of the same embodiment of the dispenser device. FIG. 1D shows a side view of the same embodiment of the dispenser device.

FIG. 3A is a partial exploded, perspective view, with a single opened storage compartment.

DETAILED DESCRIPTION

Figure 1A:
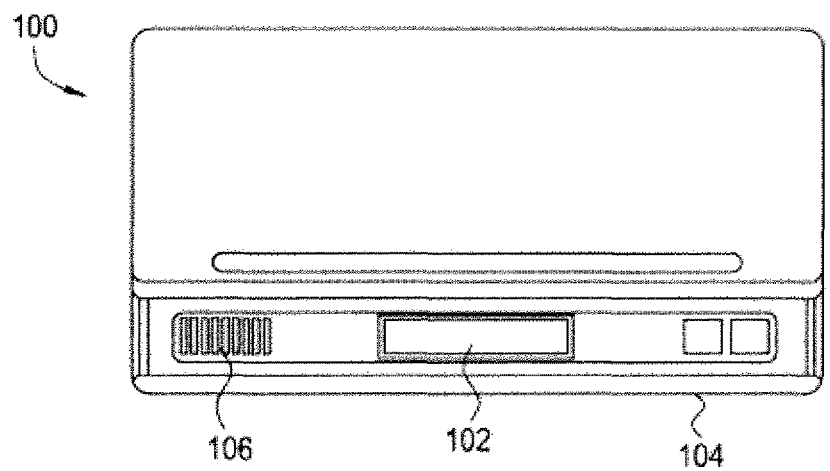
FIGS. 1A-D show a schematic diagram of one embodiment of the dispenser.

The present devices, methods, and systems, hereinafter referred to as the "PillStation System" address many of the major shortfalls in outpatient healthcare by providing a flexible central control and monitor system utilizing adaptable bandwidth image and video surveillance of a medication dispenser. As will be made apparent, some benefits of the present invention include higher compliance, ease of use, two-way communication between patient and compliance monitor (e.g., shaping patient behavior with positive reinforcement from the compliance monitor), minimizing working memory demands, additional revenue (e.g., address larger market with lower cost solutions; self-reporting services to physicians, family, others; data mining of medication/demographics), cost savings (e.g., fewer nurse visits and telephone calls), automated reporting (e.g., fast reporting, more reliable reporting about compliance, closed loop between the PillStation System and the patient), and better correlation of multiple regimen with illness. In addition, because the dispenser is based on conventional pill containers that are simple and familiar to patients and caregivers, the dispenser also has the advantage of allowing the patient or caregiver to revert to the manual use of the storage compartments upon a power failure.

The PillStation System advantageously provides direct visualization of the pills a patient is to take over a period of time. The device uses the output of a camera, CCD array, (or similar sensor and image capturing device) focused on the interior space of a storage compartment in a dispenser device, wherein the output is conveyed by ordinary telephone line, DSL, cable system, internet, cellular telephone, or other wireless network, or the like, to a central monitoring/calling system, where video screens and computer assisted observations by observers facilitate a patient's compliance with his or her prescribed medication dosage regimen. The system can provide verification that appropriate medications have been loaded in the dispenser, removed from the dispenser, and/or remain loaded in the dispenser. It also can provide surveillance from a remote location for abuse, compliance and/or diversion. Advantageously, by having a centralized system to collect and analyze the images (i.e., the compliance data), one may more cost effectively conduct the compliance monitoring, as the monitoring costs can be allocated over hundreds or thousands of patients who may be geographically scattered, since each dispenser does not have to include its own control and actuation circuitry, analytical hardware and software. The images and compliance information generated by the PillStation System are useful in clinical testing settings for preparing documentation for clinical trials necessary for submissions to the FDA.

As used herein, the terms "comprise," "comprising," "include," and "including" are intended to be open, non-limiting terms, unless the contrary is expressly indicated.
PillStation System Components The dispenser of the PillStation System is based on conventional pill containers that are simple, familiar to patients and caregivers, low cost, reusable, and capable of holding multiple medications or medication reminder markers for medications that must be taken at specific times.

In one embodiment, the device for the monitored storage and dispensing of medication includes a plurality of storage compartments, each having an interior space for storing at least one medication or at least one medication reminder marker; an image capturing device positionable to capture an image of the interior space of each of the plurality of storage compartments; and a communications module for electronically transmitting the image captured by the image capturing device to a central monitoring station. The communications module comprises conventional electronics (e.g., transmitters, processors, memory) known in the art for electronically transmitting an image or signal therefor. The device may further comprise an electronic communications component for communicating information to a user of the dispenser, from a user of the dispenser to the central monitoring station, or both to and from the user. The communications component may include at least one audio, visual, or tactile means for communicating information. Examples include LED and LCD displays, microphones, speakers, and vibration electronics. Electronics hardware and software is well known in the art for such one-way and two-way communications.

Figure 1B:
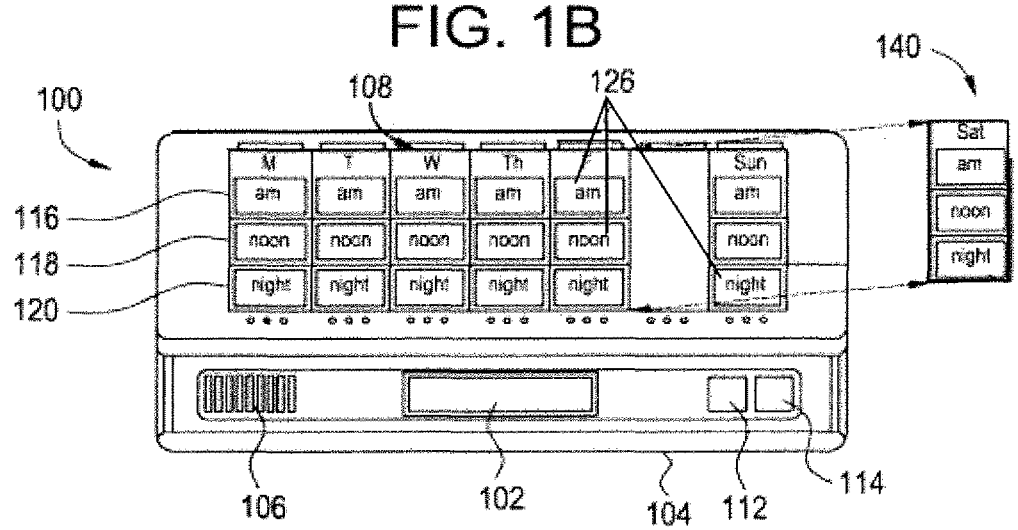
Figure 1C:
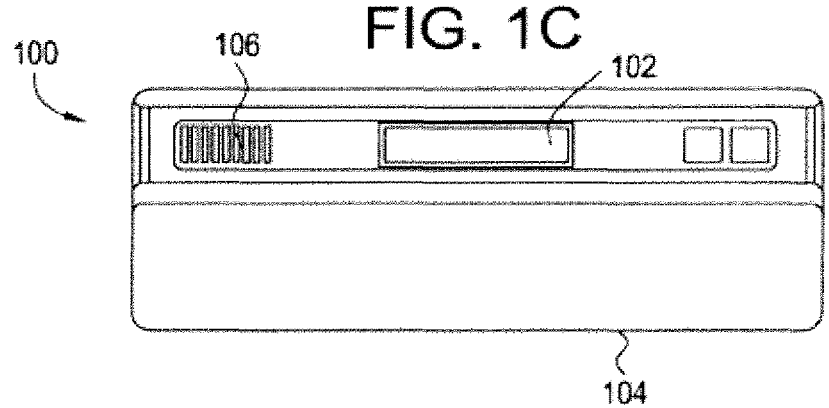
Figure 1D:
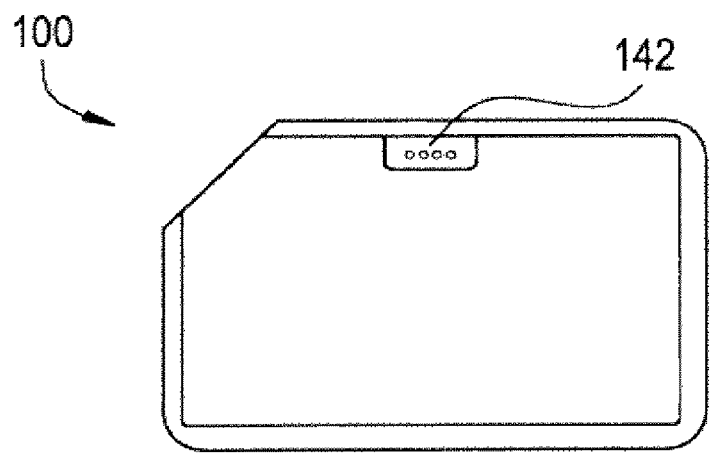

Representative, non-limiting embodiments of the dispenser device are shown in FIGS. 1A-D, FIG. 2, and FIGS. 3A and B. FIGS. 1A-D show a schematic diagram of one embodiment of the dispenser. FIG. 1A shows a top perspective view of one embodiment of the device 100 in a closed position, showing a visual display 102 for displaying information from the device to the patient, a speaker 106 for broadcasting audio signals to the patient, and a microphone 104 for telephone, voice-over IP, and for recording information from the patient or other user. FIG. 1B shows a perspective view of the same embodiment of the dispenser device 100 in an open position, showing a three-by-seven array 108 of storage compartments 126. Each storage compartment 126 typically is capable of accommodating a plurality of medications 122 or medication marker reminders. FIG. 1B shows a dispenser 100 with a weekly unit 108 of removable storage compartments 126 for accommodating up to three dosage periods per day (116, 118, and 120). Other variations of this dispenser design are envisioned, including monthly dispensers, bimonthly dispensers, and any of the foregoing with one, two, three, or four dosage periods per day. In the embodiment shown in FIG. 1B, the storage compartments 126 are removable as a single unit (e.g., as a three-by-seven array 108) or as two or more subunits 140 that correspond to one or more days of the week. FIG. 1B also shows the visual display 102 for displaying information from the device to the patient, speaker 106 for broadcasting audio signals to the patient, microphone 104 for recording information from the patient or other user, "Select" button 112, and "Call" button 114. The Select button 112 may be used to select the particular function the user desires to use (e.g., review messages, set alarm, review medication, display brightness, play music, get weather), and the Call button 114 may be used to select the particular type of call the user desires to use (e.g., call for refill, call Advisor at the central monitoring station, call pharmacy, call a family member or caregiver, leave message for the central monitoring station or pharmacy). FIG. 1C shows a bottom perspective view of the same embodiment of the dispenser device 100, showing the visual display 102 for displaying information from the device to the patient, speaker 106 for broadcasting audio signals to the patient, and microphone 104 for recording information from the patient or other user. FIG. 1D shows a side view of the same embodiment of the dispenser device, which includes a safety lock 142. It is envisioned that a safety lock may be a mechanical, electrical, or electromechanical lock as are known in the art.

Figure 2:
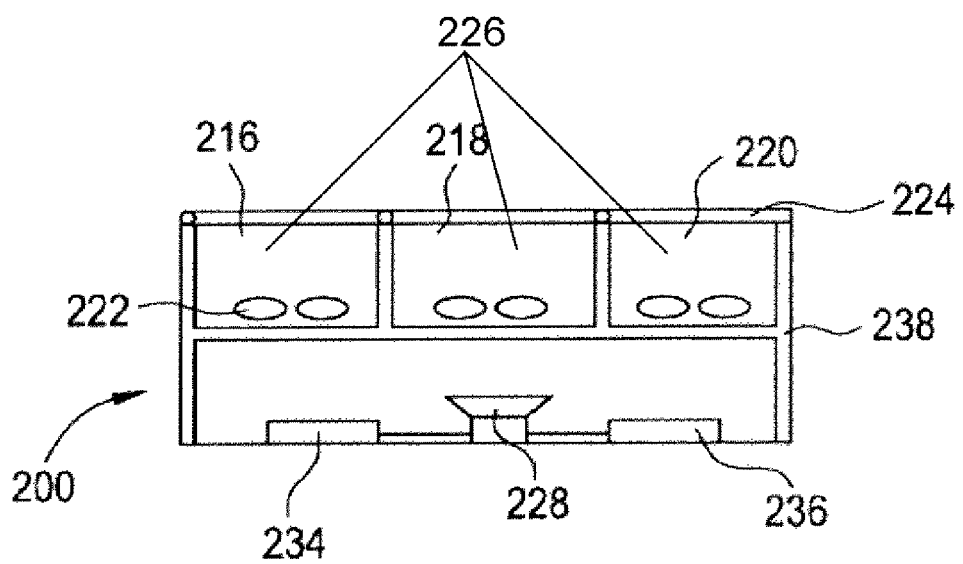
FIG. 2 shows a cross-sectional side view of one possible embodiment the device, not to scale, showing storage compartments for accommodating up to three storage dosage periods per day.

FIG. 2 shows a cross-sectional side view of another possible embodiment of the device 200, not to scale, showing a dispenser body 238 with storage compartments 226 for accommodating medications 222 or medication reminder markers for up to three storage dosage periods per day (216, 218, and 220). Each storage compartment 226 comprises a lid 224. The device 200 comprises a power source 234, a camera 228 for capturing images of the interior space of the storage compartments 226, and a network link 236 for transmitting and receiving signals from a central monitoring station.

Figure 3A:
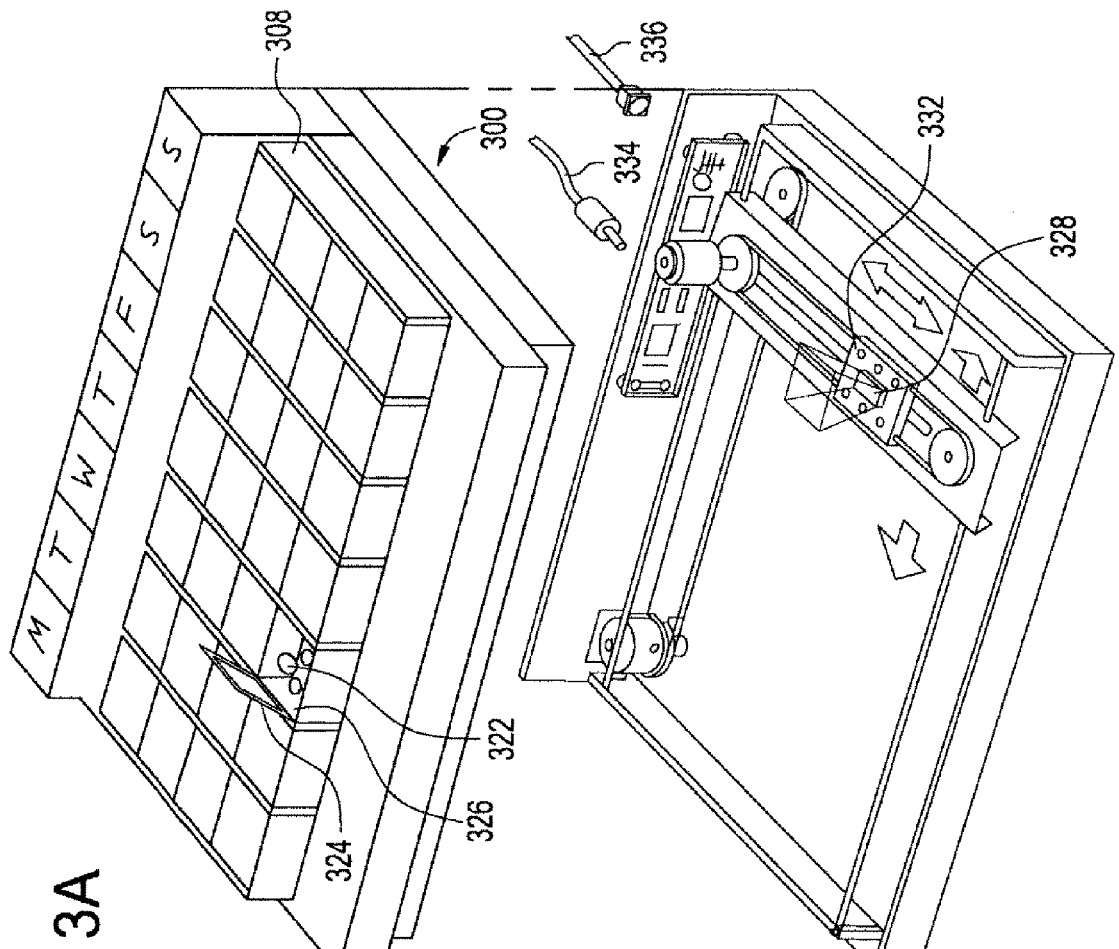
FIGS. 3A and B show a schematic diagram of one embodiment of the dispenser.
Figure 3B:
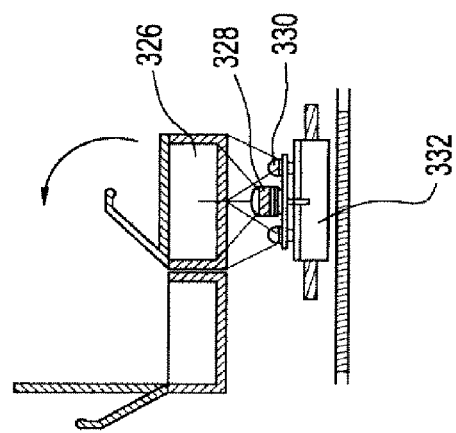
FIG. 3B is a cross-sectional view, in part, of the same embodiment of the dispenser device, showing a storage compartment with the lid opened or closed. In this embodiment, the camera is mounted to move on an X-Y platform to focus on a transparent bottom of each storage compartment. In one embodiment, each storage compartment may be selectively lighted (e.g., by an LED) to provide illumination for digital visual image capture and/or for highlighting the medication dose the patient needs to take at a particular time. It is envisioned that a camera alternatively may be mounted on a non-movable platform.

FIGS. 3A and B show a schematic diagram of another embodiment of the dispenser 300. FIG. 3A is a partial exploded, perspective view, and FIG. 3B is a cross-sectional view, in part, of the same embodiment of the dispenser device 300. In this embodiment, the camera 328 is mounted to move on an X-Y platform 332 below an array 308 of storage compartments 326 to focus on a transparent bottom of each storage compartment 326 in order to capture an image of the interior space of a storage compartment 326. Each storage compartment 326 comprises a lid 324. In one embodiment, each storage compartment may be selectively lighted (e.g., by an LED 330) to provide illumination for digital visual image capture and/or for highlighting the medication dose 322 the patient needs to take at a particular time. It is envisioned that a camera 328 alternatively may be mounted on a non-movable platform. This schematic diagram also shows the power source 334 and network link 336.

In one embodiment, the dispenser is made of an optically transparent material, such as a polymer, e.g., polycarbonate, or the like, at least in the bottom of the compartments between the medication and the image-capturing device. The bottom side of the storage compartment cover desirably may be less transparent such that the light is appropriately spread in the bin to maximize imaging results.

The image capturing device may include one or more digital still cameras, video cameras, or the like as is known in the art. The image capturing device may be oriented to view all or some of the storage compartments in the dispenser, but if less than all, then one or more additional image capturing devices typically would be included. A single camera may be provided in a fixed location within the dispenser, or the camera may be configured to move to different positions within the dispenser. The camera may include focusing means, zoom means, and/or mirrors in order to enhance image capture of each compartment or to view each compartment from different angles as needed. The camera also may comprise a polarizing filter on the lens. The images captured preferably are high resolution color images, but may be black/white. The images may be digital still images, and transmitted in various formats known in the art. The images may be high definition images. In some embodiments, the image capturing device is a video camera, capable of live monitoring of the dispenser device and/or its usage. In one embodiment, the video camera, as well as the microphone and speaker, are activated upon an audio trigger in the room where the dispenser device is located, allowing the patient to transmit questions to the central monitoring station and/or to allow the central monitoring station to guide the patient as the patient is taking his or her medications.

The storage compartments may comprise a cover that may be variously designed. In one case, it may include a design in which the cover flap protrudes outward to allow a user to insert his or her finger thereunder to flip open the flap and push the flap back, thereby opening the storage compartment cover in order to load the interior space of the storage compartment with medication or to permit removal of medication from the storage compartment. In one variation, the storage compartment is designed to facilitate ease of removal of the pill or other medication from the storage compartment. For example, the cover opening may have an additional cover extension in the storage compartment, and when the flap is pushed back, not only the cover lifts up and moves back but a bottom cover extension moves upward toward the opening, bringing the pill to the surface for ease in removal. In certain embodiments, the storage compartments are identified by a cover label or other unique marking such that the image view can easily identify if the storage compartments have been placed correctly. In certain embodiments, the lid and interior surfaces of the storage compartments are black or other suitable color to minimize reflections in the imaging.

For example, the storage compartments may have dimensions capable of hold a plurality of pills and/or larger medication delivery devices. For example, these medications may be in the form of tablets or capsules (which may be referred to as "pills"). In other embodiments, the storage compartments are dimensioned to hold other pharmaceutical dosage forms and unit dose containers. For instance, the bins may hold transdermal patches, "lollipop"-like medication sticks (which are inserted in mouth for breakthrough pain), injections, tubes, etc. For such applications where the medication may not fit properly in small storage compartments, such as those illustrated in FIG. 1B, FIG. 2, or FIG. 3A, the container comprising the multiple storage compartments may comprise different sizes and/or shapes of storage compartments, while preferably keeping the lower imaging system identical.

In other embodiments where the medication will not fit properly in the storage compartment, a medication reminder marker may be placed in the storage compartment. As used herein, a "medication reminder marker" comprises an indicator that a particular medication is to be taken at that time period corresponding to the storage compartment. The medication reminder marker may be a coin-sized chip, in one embodiment. The medication reminder marker may be made from any suitable substance compatible with the dispenser system. For example, in one embodiment, the medication reminder marker is an object made from a polymer. In preferred embodiments, the medication reminder marker has a shape and color selected to match a shape and color code present on a label of a prescribed medication. In certain embodiments, the prescribed medication is selected from the group consisting of an inhaler, a vial of an injectable medication (e.g., insulin) a parenteral, a patch, or a "lollipop"-like medication stick. The prescribed medication may be an inhaler or a parenteral medication.

The dispenser may include a display (e.g., an LED or LCD) that shows the date, time of day, or both the date and time of day, as well as for displaying messages to the user, for example, regarding compliance with the patient's medication dosage schedule. The dispenser desirably is portable and may be operated by a rechargeable battery. In one particular embodiment, the rechargeable battery may be charged using a DC adaptor. Desirably, a power LED or other signal indicates when charging is required. In one embodiment, the dispenser device comprises a speaker, through which an audio alert may be used to indicate when charging is required or to broadcast a message to the user, for example, regarding compliance with the patient's medication dosage schedule, instructions, or other information (e.g., "Please take your medications," "Please press reset button located on the side," "Medication filled or new medication added—please doublecheck," "Message from your doctor—please take this pill on an empty stomach," "You are doing excellent in taking your medications—you have not missed any doses in the last 5 days"). The dispenser device also may comprise a microphone for the user to transmit a message, for example, to the central monitoring station, physician, or pharmacy. In other embodiments, the dispenser device may be configured to be compatible with other wireless health-related devices (e.g., a blood pressure monitor), such that information from the other health-related device also may be transmitted to the central monitoring station. In addition, the dispenser device may be configured such that it is compatible with a room monitoring device (e.g., a home security system), wherein the dispenser device can monitor when a significant change takes place and notify the patient's family member and/or healthcare provider of such change.

In one embodiment, the top, storage compartment portion of the dispenser can be conveniently separated from the bottom, imaging system portion of the dispenser. This replaceably removable container may be particularly useful if the patient is traveling and desires to take the dispenser without transferring the medication. It also will facilitate washing of the compartments if necessary. The top and bottom portions of the dispenser may be releasably secured together using one or more snaps, clips, latches, or other fasteners known in the art. The storage compartments may be separated from the bottom portion of the dispenser as a single larger container, or the storage compartments may be removed as two or more subunits of the single larger container, wherein each subunit comprises two or more storage compartments. In one embodiment, the subunit corresponds to the storage compartments corresponding to at least one day of the week. In one embodiment, the subunits may be provide to the patient preloaded with a medication; the subunit storage compartments may be designed to be single use, disposable container.

In a preferred embodiment, the dispenser includes a network link via telephone line, wireless gateway (e.g., WiFi, ZigBee, Bluetooth), or cellular network which transmits processed images to a central monitor/control station. Advantageously, the network based system distributes analysis cost over the entire user base rather than packing elaborate control circuitry into each peripheral unit. The dispenser advantageously may be monitored at an alternate location when the patient is traveling, through the use of the network link as described.

The frequency and timing of calls to the camera of the PillStation System may be adjusted as needed for the particular patient and medication. For example, frequent, random calls may be scheduled to detect and deter abuse, or infrequent, regular calls may be scheduled to monitor compliance. The physician may adjust the schedule as needed.

Computer assisted operators may verify accuracy of medication loading, document compliant use of medication per physician instructions, and rule out misuse of medications that may be prone to abuse. Reports of call results may be generated and delivered to the patient, to the patient's physician, or others as desired. For example, a secure on-line compliance report may be made available for the patient's family.

In one embodiment, only one image is captured per day, stored, in-place processed, and forwarded to a gateway. This processing can be in real time or non-real time as long as there is no significant power drain.

In certain embodiments, the dispenser device comprises at least two buttons, a "Select" button and a "Call" button. The Select button may be used to select the particular function the user desires to use (e.g., review messages, set alarm, review medication, display brightness, play music, get weather), and the Call button may be used to select the particular type of call the user desires to use (e.g., call for refill, call Advisor at the central monitoring station, call pharmacy, call a family member or caregiver, leave message for the central monitoring station or pharmacy). In certain other embodiments, the dispenser device further comprises an up and/or down arrow buttons for scrolling through possible choices visually displayed on the display screen. In certain embodiments, a remote control that is configured to be compatible with the dispenser device may be used.

In another embodiment, the device comprises a security or user identification module to confirm the identity of the person accessing the contents of the storage compartments in the device. The security or user identification module may be structured such that it can detect a fingerprint, biometric shape of the user's hand or finger, or retinal scan profile. Alternatively, the module may employ voice recognition technology. In one embodiment, the camera that captures images of the interior space of the storage compartments is used to capture images of the user's finger before allowing access to the contents of the storage compartments.

As used herein, the terms "medication dosage schedule" or "medication dosage regimen" are used to describe a schedule for taking one or more prescription medications and/or one or more OTC medications. As patients often will receive prescriptions from more than one physician or specialist, the PillStation System may be used to detect the occurrence of harmful interactions between different prescription and/or OTC medications prescribed by or recommended by the multiple physicians or specialists. The PillStation may be used to prevent the harmful interactions by transmitting a signal to the patient's dispenser, which may be audibly broadcasted, e.g., from a speaker, or displayed on the visual screen. In addition or in the alternative, a computer assisted operator at the central monitoring station may contact the patient and/or his or her primary physician (e.g., by telephone, email, text message, etc.) to warn of such a possible harmful interaction. In addition, the PillStation System may be used to monitor a schedule for other health-related matters, e.g., to monitor a patient's suggested exercise regime and to provide positive reinforcement for compliance with the same.

In some embodiments, the dispenser device may be configured to automatically call the patient's pharmacy and alert the patient when a low dosage is detected. In other embodiments, the user may add a memory stick or hard drive through the USB port of the dispenser device in order to listen to music.

In one embodiment, the dispenser device may include one or more local sensors and local electronic communication components for communicating with the patient without interaction by (e.g., without going through) the central monitoring system. For example, the dispenser may locally include a sensor and microprocessor capabilities for detecting whether all of the medications have been removed from one or more of the storage compartments. The dispenser could then display or broadcast locally an alert to the user of an abnormal condition with the dispenser device or its contents. More complex processing, such as reconciling the prescribed mediation regimen with medication loaded in the storage compartments would still be conducted at the remote monitoring station via the captured images. The local detection mean can be independent of the image capture and analysis.

User Profiles

As used herein, a "patient" is a human being in need of at least one prophylactic or therapeutic medication. The term "user" is used interchangeably with the term "patient." The medication typically is a prescription medication, but also may be an over-the-counter (OTC) medication. In a preferred embodiment, each user of the PillStation System has a unique user profile which lists personal information (name, address, etc.) about the user as well as the details of their medication information, including their medication dosage schedule. Non-limiting examples of different user types may include mid-late life or elderly patients (e.g., patients with an average age of 79 years old that may suffer from multiple chronic diseases, short memory, and/or are physically challenged), patients with complex multi-medication regimens, depression patients (e.g., patients may be of any age range), child patients, and medication abuser/diverter patients. The user profile can be stored either on the device itself or at the central monitor depending on the requirements of the system. In some embodiments, the user profile also will include distinguishable physical identity information (e.g., fingerprint, biometric shape of fingers or hands, retinal scan profile) in order to ensure the patient is the one who accesses the medication in the dispenser device.

Home Installation and Use of the PillStation System

In a particular embodiment, the PillStation dispenser may be delivered to a user already on a partner gateway. The PillStation dispenser may be pre-configured for compatibility with the gateway, including all pertinent information for establishing the connection. The gateway also may be re-configured upon receipt by the user (e.g., live on-line or during past transmission). The user may link the dispenser to the gateway using any method known to those skilled in the art. For example, the user may press a button on the PillStation dispenser to enable communication between the gateway and the dispenser. Desirably, a verification of the link between the dispenser and the gateway will be provided to the user.

Such verification may be any method known in the art; non-limiting examples include an audio/voice response and/or a power LED blinking from red to green.

After establishing communication between the dispenser and the gateway, the dispenser is filled with the appropriate medications and dosages. In one embodiment, the user loads the storage compartments according to a medication dosage schedule. In other embodiments, the storage compartments are loaded by an automated dispenser, a physician, a pharmacist, caregiver, or other healthcare provider. In a particular embodiment, the user may verify that the medication has been loaded into the storage compartments appropriately. For example, the user may be required to press a button or there may be an audio prompt instructing the user to take certain steps in order for the device to capture an image and transmit it to the central monitoring station for reviewing. In another particular embodiment, the dispenser may be used to verify appropriate loading of medications and dosages. In another embodiment, the automated dispenser, physician, pharmacist, caregiver, or other healthcare provider may verify that the medication has been loaded into the storage compartments appropriately.

The PillStation dispenser may alert a user when it is time to take medication by audible, visual, or others modes of communication known in the art. For example, in one embodiment, the dispenser alerts the user by blinking and/or lighting up. In another embodiment, the dispenser may provide an audio alert to the user. In still another embodiment, the user may set time restrictions on activation of the alert system in order to avoid interruptions (e.g., the alert may be silenced through dinner).

In one embodiment, the dispenser desirably provides audio or video instructions for taking the medication (e.g., "Please take one Lipitor and one folic acid tablet with your meal."). The dispenser device may highlight the compartment from which the medication is to be withdrawn. For example, the imaging subsystem may even move to the storage compartment to show the user specifically which medication it is. The dispenser also may be used to provide messages to the user from the observers/computer operators regarding compliance with the medication dosage regimen (e.g., "Hi Mrs. Jones—you missed taking your meds yesterday—please be sure to take them today."). In another embodiment, both audio/video instructions and feedback are provided in order to shape compliance behavior. For example, a dispenser may broadcast a tone and the LED below the appropriate storage compartment may blink, starting an interval in which taking the medication will be reinforced. If the LED blinks for a 30 minute time interval, then upon removal of the medications and/or medication reminder markers from that storage compartment, the LED will glow and a message of positive reinforcement will be displayed. If the removal does not occur until after the particular time window, then there will be no glow or positive reinforcement. Instead the display message may state "Take your pills now" or "Your pills work best when taken at the right time." This pattern of reinforcement is particularly useful in shaping timely compliance behavior which is critical for many medications (e.g., medications for treating asthma, diabetes, congestive heart failure).

In addition, the dispenser device also may be used to provide messages to the user regarding other health-related issues (e.g., to remind a patient to exercise, to ask a patient to refrain from drinking, doing drugs, or gambling (for patients with known history of these diseases or habits), to ask a patient to stay away from foods high in sugar content (for patients with diabetes), to ask a patient not to go outside in cold temperatures (for patients with arthritis, to remind a patient of appointment times, etc.).

In one embodiment, the user (or his/her family or caregiver) can go on-line and view an image of their pill dispenser and their prescriptions. The user also may be able to review what pills need to taken and when the pills need to be taken. In addition, the user and/or their family or caregiver can perform various functions by visiting an online page and/or by sending email instructions. (e.g., registering, billing, creating profiles, setting preferences, setting alarms, view call logs, view compliance report, view messages to the users, view frequently asked questions, view medication input, communicate with the compliance monitoring station).

In one embodiment, the dispenser hardware and electronics are tamper resistant or tamper proof. The device may comprise a child safety lock, to prevent a child's access to the medication storage compartments. In some embodiments, when tampering occurs, the patient is alerted by a message transmitted to the local computer, land-line telephone line, cellular phone, or as a text message.

In one embodiment, the dispenser device can join in a telephone call in progress, when requested by the patient by making a particular keystroke (e.g., if user and caregiver are talking, they can press a particular combination of buttons, and the dispenser device will "wake up" and can give compliance status to both parties on call, allowing the caregiver to share the data directly from the pill station in the middle of the call.).

Monitoring of the PillStation Dispenser

Figure 4:
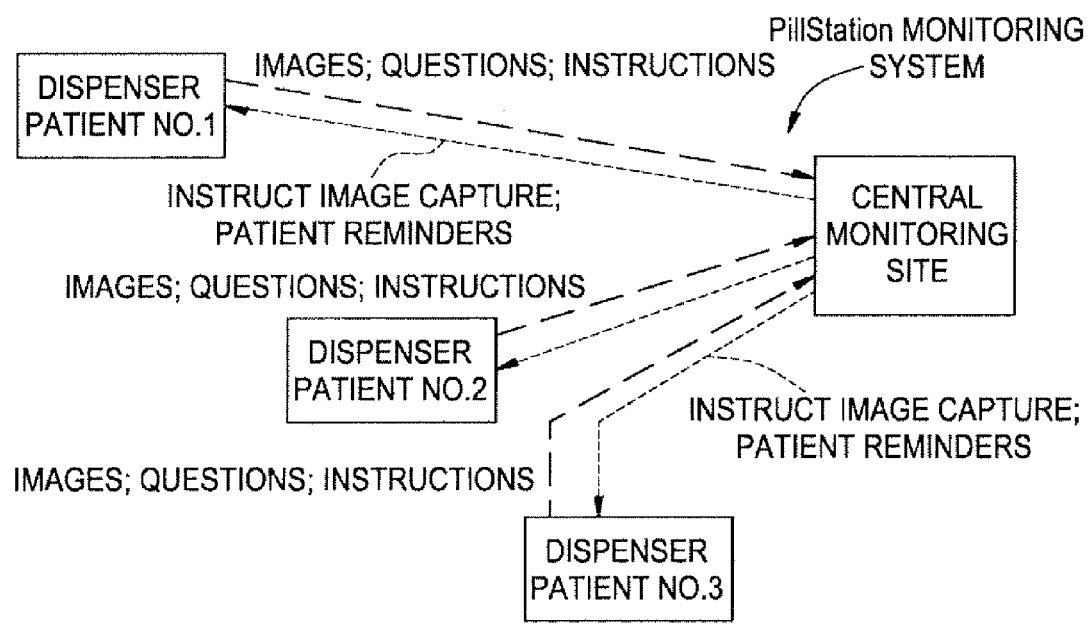
FIG. 4 shows a process flow diagram, illustrating how one embodiment of the compliance monitoring system would work.

Medication compliance is monitored by the PillStation dispenser using an image capturing device, such as inexpensive camera or similar device, to capture images of the medication or medication reminder marker and thereafter upload the images to the gateway as shown schematically in FIG. 4. The image may be compressed or otherwise processed as known in the art to facilitate electronic transmission of images. In one embodiment, the camera is capable of visualizing a font size of 6 on the medication. In another embodiment, the camera is capable of visualizing medications of different colors, shapes, and sizes. For example, the camera desirably may be designed and oriented in relation to the dispenser bins in order to be capable of visualizing small medications that are approximately 6.0 mm in diameter having markings of approximately 1.0 mm high and approximately 0.6 mm wide.

In another embodiment, the medications may have numbers inscribed across the top/bottom surface such that some of the exposed numbers can be resolved. In one example, these inscribed numbers may be on a white pill. In one embodiment of the dispenser device, the camera is capable of visualizing these inscribed numbers through the bottom of the dispenser. The dispenser and camera may be designed to utilize ambient light (e.g., from the room in which the use locates the dispenser) in the image capturing process. Alternatively or in addition, the dispenser may include a flash, LED, or other illumination source built into the dispenser, e.g., located in the bottom of the dispenser to emit light into each of the bins to be imaged. The illumination source may be movable, e.g., with a selectively positionable camera.

In one embodiment, a reference mark on the bottom of the dispenser is used to pre-calculate an "area of interest" upon start of the scan/imaging, permitting only the area of interest to be imaged and other areas discarded. This reference mark calibration may be required only infrequently, depending on the electro/mechanical assembly tolerance shifts over time.

The dispenser communicates with the central monitor through means such as wireless communication, telephone communication, or through a cellular network. Those of ordinary skill in the art will appreciate that different adapters may be required for each type of communication (e.g., WiFi dongle, zigbee dongle, powerline dongle, bluetooth dongle). Desirably, the communication adapter is connected to the PillStation dispenser through a USB interface, thereby allowing different kinds of hardware to be interchanged more easily. The dispenser desirably self-detects the adapter and configures appropriately to the network. In a particular embodiment, if a USB adapter driver is not available, an option may be available to insert a USB memory stick with the drivers with only the required adapter being loaded.

In one embodiment, the images captured by the PillStation dispenser originally are stored in local memory and then transmitted to the central monitoring station. At the central monitoring station, image recognition software (e.g., OCR and other software) may be utilized to determine the type/number of pills left. Each PillStation dispenser preferably has a unique ID number and a password, allowing the PillStation dispenser to be linked automatically to the correct user profile and medication dosage schedule. The data analyzed by the image recognition software then may be compared to the user's profile medication dosage schedule to determine the user's compliance in taking medication.

In certain embodiments, an observer at the central monitoring station monitors the patient's dispensers to determine the patient's compliance with his or her medication dosage schedule. The monitoring center may be located in a time zone shifted about 12 hours for the patient population, so that observers working a day shift could monitor the patients' dispensers when the patients are typically asleep. In certain embodiments, if the observer observes a major error in compliance with the user's dosage medication schedule, the observer will notify the user and/or a second observer that may communicate with the user. If the error in compliance cannot be resolved, the second observer may notify a pharmacist who may review the error and consult the user, user's physician, family member, and/or insurance provider.

The data (i.e., captured images) may be collected as frequently and/or randomly as needed as determined by the physician and the gateway/central monitoring station. Non-limiting examples of supported modes for data collection include once per day at a time to be determined, many times a day at a time to be determined, or randomly with a settable frequency. In one embodiment, the frequency of image capture may decrease when the battery power is low.

In certain embodiments, if the captured image transmitted to the central monitoring station matches what is expected for the patient's medication dosage schedule, information is transmitted to the dispenser for positive reinforcement (e.g., "Great job, Ms. Jones!"). Positive reinforcement may be continuous (i.e., after each dosage is taken on time), or intermittent (i.e., variable time between operator full monitors, to be done randomly, to reward compliance with dosage medication schedule without errors in time, omissions, or overuse). In certain other embodiments, when the captured image transmitted to the monitoring station does not match what is expected for the patient's medication dosage schedule, the central monitoring station transmits personalized instructions about the medication error to the dispenser device. The instructions may be visually displayed on the display screen and/or audibly broadcast. In certain other embodiments, if such a medication error is repeated for one or more times, the central monitoring station may transmit a signal/message to the patient's caregiver, physician, or other healthcare provider.

In another embodiment, the dispenser device is able to detect if a medication or medication reminder marker is present in a storage compartment or if the storage compartment is empty (i.e., if all medications were taken from the storage compartment), and can transmit a message to the patient if less than all of the medications or markers were removed.

Medication Image Processing

In a preferred embodiment, the image transmitted to the central monitor from the camera is minimally compressed. In various embodiments, several processing/analysis algorithms may be executed to further reduce the image size. For example, the image processing may include:

1. Discard images of empty bins—Each bin can be processed separately and upon an empty bin signature, that image need not be kept. Also, through historical trend as well as knowledge of the prescription ID number and the number and types of pills that need to be taken, one can verify the location and day of empty bins.
2. Discard images with no change—If there is a strong correlation between last image and current one, then this data can be discarded as well.
3. Image cropping—Only the image of the bin with area of interest is required hence other segments of the images can be discarded.
4. Lossless image compression: For some of the bins some simple lossless compression may be required.

The present invention has numerous advantages over prior art dispensing devices and monitoring systems. Such advantages include verification that appropriate medications have been loaded into the dispenser, surveillance for both abuse and non-adherence, reduced costs, and behavioral modification with positive reinforcement.

For processed images which still are below the acceptable threshold confidence factor (of types, number, etc. of medications as specified in Rx or expected), these images may be sent to a central operator. These operators can view storage compartment images alongside names and reference images of pills that should be in the bin, such that comparisons between the image received and the expected image can be made rapidly. To maintain quality control, test images may be inserted and operator performance can be monitored in real-time. Such a system can be used for operator training as well.

It should be apparent that the foregoing relates only to exemplary embodiments of the present invention, and that numerous changes and modifications may be made therein without departing from the scope of the invention as defined by the following claims.

We claim:

1. A device for the monitored storage and dispensing of medication to a user comprising:
    a plurality of user-accessible storage compartments, wherein each storage compartment has an interior space for storing at least one medication or at least one medication reminder marker, and wherein the plurality of user-accessible storage compartments are presented and arranged together in order of a medication dosage schedule in which the at least one medication or the at least one medication reminder marker is to be removed from each of the plurality of user-accessible storage compartment by the user;
    an image capturing device configured to capture at least one image of the interior space of the plurality of user-accessible storage compartments; and
    a communications module for electronically transmitting the image captured by the image capturing device to a central monitoring station.

2. The device of claim 1, wherein each user-accessible storage compartment comprises a wall through which the image can be captured, for direct visualization of any medication or medication reminder marker within the interior space of the user-accessible storage compartment.

3. The device of claim 1, wherein the plurality of user-accessible storage compartments is provided in an array corresponding to the days of the week and periods of time throughout the day.

4. The device of claim 1, wherein the plurality of user-accessible storage compartments are replaceably removable from the device.

5. The device of claim 4, wherein the plurality of user-accessible storage compartments are removable in two or more subunits of two or more storage compartments.

6. The device of claim 5, wherein each subunit comprises storage compartments corresponding to at least one day of the week.

7. The device of claim 1, wherein the image capturing device comprises a stationary camera.

8. The device of claim 7, wherein the camera comprises a digital still camera or a digital video camera.

9. The device of claim 1, wherein the communications module for electronically transmitting at least a portion of the captured image comprises a network link for a telephone line, power line, wireless gateway, or cellular network.

10. The device of claim 9, wherein the network link comprises an embedded or dongle circuitry for WiFi, zigbee, powerline, or bluetooth transmission circuitry.

11. The device of claim 1, further comprising an electronic communications component for communicating information to a user of the dispenser, from a user of the dispenser to the central monitoring station, or both to and from the user.

12. The device of claim 11, wherein the information communicated to the user comprises battery power level or other operational status information about the device.

13. The device of claim 11, wherein the information communicated to the user comprises information about the user's compliance with his or her medication dosage schedule.

14. The device of claim 11, wherein the information communicated from a user of the dispenser to the central monitoring station comprises personal identity information of the user of the dispenser.

15. A patient medication compliance monitoring system comprising:
at least one visually monitored medication dispenser assigned to an individual patient having a medication dosage schedule, wherein the medication dispenser comprises (i) a plurality of user-accessible storage compartments, wherein each compartment has an interior space for storing at least one medication or medication reminder marker, and wherein the plurality of user-accessible storage compartments are presented and arranged together in order of a medication dosage schedule in which the at least one medication or the at least one medication reminder marker is to be removed from each of the plurality of user-accessible storage compartment by the user, (ii) an image capturing device configured to capture at least one image of the interior space of the plurality of user-accessible storage compartments, and (iii) a communications module for electronically transmitting the image captured by the image capturing device to a central monitoring station; and
a central monitoring station that is capable of receiving and viewing the image transmitted from the at least one medication dispenser.

16. The compliance monitoring system of claim 15, comprising a plurality of visually monitored medication dispensers, wherein each medication dispenser is assigned to a different individual patient having a medication dosage schedule.

17. The compliance monitoring system of claim 15, wherein the image capturing device comprises a stationary camera, and the communications module for electronically transmitting the captured image comprises a network link for a telephone line, wireless gateway, or cellular network.

18. The compliance monitoring system of claim 15, wherein the medication dispenser further comprises an electronic communications component for communicating information to a user of the dispenser, from a user of the dispenser to the central monitoring station, or both to and from the user.

19. The compliance monitoring system of claim 15, wherein the medication dispenser is adapted to receive image capture instructions from the central monitoring station.

20. The compliance monitoring system of claim 15, which comprises the use of at least one computer.

* * * * *